US012201821B2

United States Patent
Schlebusch et al.

(10) Patent No.: US 12,201,821 B2
(45) Date of Patent: Jan. 21, 2025

(54) METHOD FOR DETERMINING A FLOW RATE OF A FLUID FLOWING THROUGH AN IMPLANTED VASCULAR SUPPORT SYSTEM, AND IMPLANTABLE VASCULAR SUPPORT SYSTEM

(71) Applicant: KARDION GMBH, Stuttgart (DE)

(72) Inventors: Thomas Alexander Schlebusch, Renningen (DE); Tobias Schmid, Stuttgart (DE)

(73) Assignee: KARDION GMBH, Stuttgart (DE)

( * ) Notice: Subject to any disclaimer, the term of this patent is extended or adjusted under 35 U.S.C. 154(b) by 1080 days.

(21) Appl. No.: 15/734,353

(22) PCT Filed: Jun. 6, 2019

(86) PCT No.: PCT/EP2019/064804
§ 371 (c)(1),
(2) Date: Jul. 16, 2021

(87) PCT Pub. No.: WO2019/234164
PCT Pub. Date: Dec. 12, 2019

(65) Prior Publication Data
US 2021/0346676 A1     Nov. 11, 2021

(30) Foreign Application Priority Data
Jun. 6, 2018   (DE) .......................... 102018208929.9

(51) Int. Cl.
*A61M 60/178*    (2021.01)
*A61M 60/216*    (2021.01)
(Continued)

(52) U.S. Cl.
CPC ........ *A61M 60/178* (2021.01); *A61M 60/216* (2021.01); *A61M 60/523* (2021.01);
(Continued)

(58) Field of Classification Search
CPC ........... A61B 8/488; A61B 8/06; A61B 8/065; A61B 8/0891; A61M 60/178;
(Continued)

(56) References Cited

U.S. PATENT DOCUMENTS

| 3,088,323 A | 5/1963 | Welkowitz et al. |
| 4,023,562 A | 5/1977 | Hynecek et al. |

(Continued)

FOREIGN PATENT DOCUMENTS

| CA | 3 122 415 | 7/2020 |
| CN | 1192351 A | 9/1998 |

(Continued)

OTHER PUBLICATIONS

Atkinson et al., "Pulse-Doppler Ultrasound and Its Clinical Application", The Yale Journal of Biology and Medicine, 1977, vol. 50, pp. 367-373.

(Continued)

*Primary Examiner* — Colin T. Sakamoto
*Assistant Examiner* — Tommy T Ly
(74) *Attorney, Agent, or Firm* — Knobbe, Martens, Olson & Bear, LLP (57) ABSTRACT

The invention relates to a method for determining a flow rate of a fluid flowing through an implanted vascular assist system (1), said method comprising the following steps: a) carrying out a first pulsed Doppler measurement at a first pulse repetition rate by means of an ultrasonic sensor (2) of the assist system (1); b) carrying out a second pulsed Doppler measurement at a second pulse repetition rate by means of the ultrasonic sensor (2) of the assist system (1), wherein the second pulse repetition rate differs from the first pulse repetition rate; c) determining the flow rate using measurement results of the first pulsed Doppler measurement and the second pulsed Doppler measurement.

13 Claims, 3 Drawing Sheets

(51) Int. Cl.
*A61M 60/523* (2021.01)
*A61M 60/816* (2021.01)

(52) U.S. Cl.
CPC ... *A61M 60/816* (2021.01); *A61M 2205/3334* (2013.01); *A61M 2210/125* (2013.01)

(58) Field of Classification Search
CPC .............. A61M 60/216; A61M 60/523; A61M 60/816; A61M 2205/3334; A61M 2210/125
See application file for complete search history.

(56) References Cited

U.S. PATENT DOCUMENTS

| | | | |
|---|---|---|---|
| 4,559,952 A | 12/1985 | Angelsen et al. |
| 4,781,525 A | 11/1988 | Hubbard et al. |
| 4,888,011 A | 12/1989 | Kung et al. |
| 4,889,131 A | 12/1989 | Salem et al. |
| 4,902,272 A | 2/1990 | Milder et al. |
| 5,045,051 A | 9/1991 | Milder et al. |
| 5,269,811 A | 12/1993 | Hayes |
| 5,289,821 A | 3/1994 | Swartz |
| 5,456,715 A | 10/1995 | Liotta |
| 5,527,159 A | 6/1996 | Bozeman, Jr. et al. |
| 5,581,038 A | 12/1996 | Lampropoulos |
| 5,613,935 A | 3/1997 | Jarvik |
| 5,662,115 A | 9/1997 | Torp |
| 5,676,651 A | 10/1997 | Larson, Jr. et al. |
| 5,720,771 A | 2/1998 | Snell |
| 5,752,976 A | 5/1998 | Duffin et al. |
| 5,766,207 A | 6/1998 | Potter et al. |
| 5,827,203 A | 10/1998 | Nita |
| 5,888,242 A | 3/1999 | Antaki et al. |
| 5,904,708 A | 5/1999 | Goedeke |
| 5,911,685 A | 6/1999 | Siess et al. |
| 5,964,694 A | 10/1999 | Siess et al. |
| 5,980,465 A | 11/1999 | Elgas |
| 6,007,478 A | 12/1999 | Siess et al. |
| 6,024,704 A | 2/2000 | Meador et al. |
| 6,053,873 A | 4/2000 | Govari et al. |
| 6,176,822 B1 | 1/2001 | Nix et al. |
| 6,183,412 B1 | 2/2001 | Benkowsi et al. |
| 6,185,460 B1 | 2/2001 | Thompson |
| 6,190,324 B1 | 2/2001 | Kieval et al. |
| 6,210,318 B1 | 4/2001 | Lederman |
| 6,231,498 B1 | 5/2001 | Pfeiffer et al. |
| 6,245,007 B1 | 6/2001 | Bedingham et al. |
| 6,314,322 B1 | 11/2001 | Rosenberg |
| 6,351,048 B1 | 2/2002 | Schob et al. |
| 6,398,734 B1 | 6/2002 | Cimochowski et al. |
| 6,432,136 B1 | 8/2002 | Weiss et al. |
| 6,438,409 B1 | 8/2002 | Malik et al. |
| 6,512,949 B1 | 1/2003 | Combs et al. |
| 6,530,876 B1 | 3/2003 | Spence |
| 6,540,658 B1 | 4/2003 | Fasciano et al. |
| 6,540,659 B1 | 4/2003 | Milbocker |
| 6,561,975 B1 | 5/2003 | Pool et al. |
| 6,579,257 B1 | 6/2003 | Elgas et al. |
| 6,602,182 B1 | 8/2003 | Milbocker |
| 6,605,032 B2 | 8/2003 | Benkowsi et al. |
| 6,652,447 B2 | 11/2003 | Benkowsi et al. |
| 6,731,976 B2 | 5/2004 | Penn et al. |
| 6,879,126 B2 | 4/2005 | Paden et al. |
| 6,912,423 B2 | 6/2005 | Ley et al. |
| 6,949,066 B2 | 9/2005 | Bearnson et al. |
| 6,984,201 B2 | 1/2006 | Khaghani et al. |
| 7,022,100 B1 | 4/2006 | Aboul-Hosn et al. |
| 7,024,244 B2 | 4/2006 | Muhlenberg et al. |
| 7,070,555 B2 | 7/2006 | Siess |
| 7,083,588 B1 | 8/2006 | Shmulewitz et al. |
| 7,138,776 B1 | 11/2006 | Gauthier et al. |
| 7,160,243 B2 | 1/2007 | Medvedev |
| 7,175,588 B2 | 2/2007 | Morello |
| 7,177,681 B2 | 2/2007 | Xhu |
| 7,238,151 B2 | 7/2007 | Frazier |
| 7,396,327 B2 | 7/2008 | Morello |
| 7,513,864 B2 | 4/2009 | Kantrowitz et al. |
| 7,520,850 B2 | 4/2009 | Brockway |
| 7,591,777 B2 | 9/2009 | LaRose |
| 7,744,560 B2 | 6/2010 | Struble |
| 7,794,384 B2 | 9/2010 | Sugiura et al. |
| 7,819,916 B2 | 10/2010 | Yaegashi |
| 7,850,593 B2 | 12/2010 | Vincent et al. |
| 7,850,594 B2 | 12/2010 | Sutton et al. |
| 7,856,335 B2 | 12/2010 | Morello et al. |
| 7,862,501 B2 | 1/2011 | Woodward et al. |
| 7,951,062 B2 | 5/2011 | Morello |
| 7,951,129 B2 | 5/2011 | Chinchoy |
| 7,963,905 B2 | 6/2011 | Salmonsen et al. |
| 7,988,728 B2 | 8/2011 | Ayre |
| 8,075,472 B2 | 12/2011 | Zilbershlag et al. |
| 8,190,390 B2 | 5/2012 | Morello et al. |
| 8,211,028 B2 | 7/2012 | Karamanoglu et al. |
| 8,303,482 B2 | 11/2012 | Schima et al. |
| 8,323,173 B2 | 12/2012 | Benkowsi et al. |
| 8,435,182 B1 | 5/2013 | Tamura |
| 8,449,444 B2 | 5/2013 | Poirier |
| 8,545,380 B2 | 10/2013 | Farnan et al. |
| 8,585,572 B2 | 11/2013 | Mehmanesh |
| 8,591,393 B2 | 11/2013 | Walters et al. |
| 8,594,790 B2 | 11/2013 | Kjellstrom et al. |
| 8,622,949 B2 | 1/2014 | Zafirelis et al. |
| 8,657,733 B2 | 2/2014 | Ayre et al. |
| 8,657,875 B2 | 2/2014 | Kung et al. |
| 8,715,151 B2 | 5/2014 | Poirier |
| 8,747,293 B2 | 6/2014 | Arndt et al. |
| 8,849,398 B2 | 9/2014 | Evans |
| 8,864,643 B2 | 10/2014 | Reichenbach et al. |
| 8,864,644 B2 | 10/2014 | Yomtov |
| 8,876,685 B2 | 11/2014 | Crosby et al. |
| 8,882,477 B2 | 11/2014 | Fritz, IV et al. |
| 8,888,728 B2 | 11/2014 | Aboul-Hosn et al. |
| 8,897,873 B2 | 11/2014 | Schima et al. |
| 8,903,492 B2 | 12/2014 | Soykan et al. |
| 9,091,271 B2 | 7/2015 | Bourque |
| 9,297,735 B2 | 3/2016 | Graichen et al. |
| 9,308,305 B2 | 4/2016 | Chen et al. |
| 9,345,824 B2 | 5/2016 | Mohl et al. |
| 9,371,826 B2 | 6/2016 | Yanai et al. |
| 9,427,508 B2 | 8/2016 | Reyes et al. |
| 9,474,840 B2 | 10/2016 | Siess |
| 9,492,601 B2 | 11/2016 | Casas et al. |
| 9,511,179 B2 | 12/2016 | Casas et al. |
| 9,555,173 B2 | 1/2017 | Spanier |
| 9,555,175 B2 | 1/2017 | Bulent et al. |
| 9,556,873 B2 | 1/2017 | Yanai et al. |
| 9,566,374 B2 | 2/2017 | Spence et al. |
| 9,636,442 B2 | 5/2017 | Karmon et al. |
| 9,656,010 B2 | 5/2017 | Burke |
| 9,669,142 B2 | 6/2017 | Spanier et al. |
| 9,669,144 B2 | 6/2017 | Spanier et al. |
| 9,694,123 B2 | 7/2017 | Bourque et al. |
| 9,713,701 B2 | 7/2017 | Sarkar et al. |
| 9,744,282 B2 | 8/2017 | Rosenberg et al. |
| 9,833,550 B2 | 12/2017 | Siess |
| 9,848,899 B2 | 12/2017 | Sliwa et al. |
| 9,849,224 B2 | 12/2017 | Angwin et al. |
| 9,878,087 B2 | 1/2018 | Richardson et al. |
| 9,943,236 B2 | 4/2018 | Bennett et al. |
| 9,950,102 B2 | 4/2018 | Spence et al. |
| 9,974,894 B2 | 5/2018 | Morello |
| 9,999,714 B2 | 6/2018 | Spanier et al. |
| 10,010,662 B2 | 7/2018 | Wiesener et al. |
| 10,022,480 B2 | 7/2018 | Greatrex et al. |
| 10,029,037 B2 | 7/2018 | Muller et al. |
| 10,052,420 B2 | 8/2018 | Medvedev et al. |
| 10,279,093 B2 | 5/2019 | Reichenbach et al. |
| 10,322,217 B2 | 6/2019 | Spence |
| 10,342,906 B2 | 7/2019 | D'Ambrosio et al. |
| 10,350,342 B2 | 7/2019 | Thomas et al. |
| 10,357,598 B2 | 7/2019 | Aboul-Hosn et al. |
| 10,376,162 B2 | 8/2019 | Edelman et al. |
| 10,413,651 B2 | 9/2019 | Yomtov et al. |

(56) References Cited

U.S. PATENT DOCUMENTS

| | | |
|---|---|---|
| 10,426,879 B2 | 10/2019 | Farnan |
| 10,449,275 B2 | 10/2019 | Corbett |
| 10,500,322 B2 | 12/2019 | Karch |
| 10,525,178 B2 | 1/2020 | Zeng |
| 10,549,020 B2 | 2/2020 | Spence et al. |
| 10,561,771 B2 | 2/2020 | Heilman et al. |
| 10,561,772 B2 | 2/2020 | Schumacher |
| 10,561,773 B2 | 2/2020 | Ferrari et al. |
| 10,632,241 B2 | 4/2020 | Schenck et al. |
| 10,660,998 B2 | 5/2020 | Hodges |
| 10,668,195 B2 | 6/2020 | Flores |
| 10,732,583 B2 | 8/2020 | Rudser |
| 10,857,275 B2 | 12/2020 | Granegger |
| 11,027,114 B2 | 6/2021 | D'Ambrosio et al. |
| RE48,649 E | 7/2021 | Siess |
| 11,067,085 B2 | 7/2021 | Granegger et al. |
| 11,120,908 B2 | 9/2021 | Agnello et al. |
| 11,131,968 B2 | 9/2021 | Rudser |
| 11,147,960 B2 | 10/2021 | Spanier et al. |
| 11,154,701 B2 | 10/2021 | Reyes et al. |
| 11,154,702 B2 | 10/2021 | Kadrolkar et al. |
| 11,185,682 B2 | 11/2021 | Farnan |
| 11,191,945 B2 | 12/2021 | Siess et al. |
| 11,197,618 B2 | 12/2021 | Edelman et al. |
| 11,217,344 B2 | 1/2022 | Agnello |
| 11,235,139 B2 | 2/2022 | Kudlik |
| 11,241,572 B2 | 2/2022 | Dague et al. |
| 11,273,299 B2 | 3/2022 | Wolman et al. |
| 11,285,310 B2 | 3/2022 | Curran et al. |
| 11,285,311 B2 | 3/2022 | Siess et al. |
| 11,298,524 B2 | 4/2022 | El Katerji et al. |
| 11,311,711 B2 | 4/2022 | Casas et al. |
| 11,316,679 B2 | 4/2022 | Agnello |
| 11,320,382 B2 | 5/2022 | Aikawa |
| 11,324,395 B2 | 5/2022 | Banik et al. |
| 11,331,082 B2 | 5/2022 | Itoh et al. |
| 11,337,724 B2 | 5/2022 | Masubuchi et al. |
| 11,338,125 B2 | 5/2022 | Liu et al. |
| 11,351,356 B2 | 6/2022 | Mohl |
| 11,351,357 B2 | 6/2022 | Mohl |
| 11,351,358 B2 | 6/2022 | Nix et al. |
| 11,357,438 B2 | 6/2022 | Stewart et al. |
| 11,357,968 B2 | 6/2022 | El Katerji et al. |
| 11,376,415 B2 | 7/2022 | Mohl |
| 11,376,419 B2 | 7/2022 | Reyes et al. |
| 11,389,639 B2 | 7/2022 | Casas |
| 11,389,641 B2 | 7/2022 | Nguyen et al. |
| 11,413,444 B2 | 8/2022 | Nix et al. |
| 11,413,445 B2 | 8/2022 | Brown et al. |
| 11,420,041 B2 | 8/2022 | Karch |
| 11,439,806 B2 | 9/2022 | Kimball et al. |
| 11,446,481 B2 | 9/2022 | Wolman et al. |
| 11,478,629 B2 | 10/2022 | Harjes et al. |
| 11,517,740 B2 | 12/2022 | Agarwa et al. |
| 11,521,723 B2 | 12/2022 | Liu et al. |
| 11,524,165 B2 | 12/2022 | Tan et al. |
| 11,527,322 B2 | 12/2022 | Agnello et al. |
| 11,529,062 B2 | 12/2022 | Moyer et al. |
| 11,554,260 B2 | 1/2023 | Reyes et al. |
| 11,572,879 B2 | 2/2023 | Mohl |
| 11,574,741 B2 | 2/2023 | Tan et al. |
| 11,577,068 B2 | 2/2023 | Spence et al. |
| 11,581,083 B2 | 2/2023 | El Katerji et al. |
| 11,583,659 B2 | 2/2023 | Pfeffer et al. |
| 11,587,337 B2 | 2/2023 | Lemay et al. |
| 11,590,337 B2 | 2/2023 | Granegger et al. |
| 11,622,695 B1 | 4/2023 | Adriola et al. |
| 11,628,293 B2 | 4/2023 | Gandhi et al. |
| 11,639,722 B2 | 5/2023 | Medvedev et al. |
| 11,648,386 B2 | 5/2023 | Poirer |
| 11,653,841 B2 | 5/2023 | Reyes et al. |
| 11,666,746 B2 | 6/2023 | Ferrari et al. |
| 11,668,321 B2 | 6/2023 | Richert et al. |
| 11,674,517 B2 | 6/2023 | Mohl |
| 11,676,718 B2 | 6/2023 | Agnello et al. |
| 11,684,276 B2 | 6/2023 | Cros et al. |
| 11,684,769 B2 | 6/2023 | Harjes et al. |
| 11,694,539 B2 | 7/2023 | Kudlik et al. |
| 11,694,813 B2 | 7/2023 | El Katerji et al. |
| 11,696,782 B2 | 7/2023 | Carlson et al. |
| 11,707,617 B2 | 7/2023 | Reyes et al. |
| 11,712,167 B2 | 8/2023 | Medvedev et al. |
| 11,754,077 B1 | 9/2023 | Mohl |
| D1,001,145 S | 10/2023 | Lussier et al. |
| D1,001,146 S | 10/2023 | Lussier et al. |
| 11,771,885 B2 | 10/2023 | Liu et al. |
| 11,779,234 B2 | 10/2023 | Harjes et al. |
| 11,781,551 B2 | 10/2023 | Yanai et al. |
| 11,790,487 B2 | 10/2023 | Barbato et al. |
| 11,793,994 B2 | 10/2023 | Josephy et al. |
| 11,806,116 B2 | 11/2023 | Tuval et al. |
| 11,806,517 B2 | 11/2023 | Petersen |
| 11,806,518 B2 | 11/2023 | Michelena et al. |
| 11,813,079 B2 | 11/2023 | Lau et al. |
| 11,818,782 B2 | 11/2023 | Doudian et al. |
| 11,824,381 B2 | 11/2023 | Conyers et al. |
| 11,826,127 B2 | 11/2023 | Casas |
| 11,832,793 B2 | 12/2023 | McWeeney et al. |
| 11,832,868 B2 | 12/2023 | Smail et al. |
| 11,837,364 B2 | 12/2023 | Lee et al. |
| 11,844,592 B2 | 12/2023 | Tuval et al. |
| 11,844,940 B2 | 12/2023 | D'Ambrosio et al. |
| 11,850,073 B2 | 12/2023 | Wright et al. |
| 11,850,414 B2 | 12/2023 | Schenck et al. |
| 11,850,415 B2 | 12/2023 | Schwammenthal et al. |
| D1,012,284 S | 1/2024 | Glaser et al. |
| 11,857,345 B2 | 1/2024 | Hanson et al. |
| 11,864,878 B2 | 1/2024 | Duval et al. |
| 11,872,384 B2 | 1/2024 | Cotter |
| 11,883,207 B2 | 1/2024 | El Katerji et al. |
| D1,014,552 S | 2/2024 | Lussier et al. |
| 11,890,082 B2 | 2/2024 | Cros et al. |
| 11,896,199 B2 | 2/2024 | Lent et al. |
| 11,900,660 B2 | 2/2024 | Saito et al. |
| 11,903,657 B2 | 2/2024 | Geric et al. |
| 11,906,411 B2 | 2/2024 | Graichen et al. |
| 11,911,550 B2 | 2/2024 | Itamochi et al. |
| D1,017,634 S | 3/2024 | Lussier et al. |
| D1,017,699 S | 3/2024 | Moore et al. |
| 11,923,078 B2 | 3/2024 | Fallen et al. |
| 11,923,093 B2 | 3/2024 | Moffitt et al. |
| 11,925,794 B2 | 3/2024 | Malkin et al. |
| 11,931,073 B2 | 3/2024 | Walsh et al. |
| 11,931,528 B2 | 3/2024 | Rohl et al. |
| 11,931,588 B2 | 3/2024 | Aghassian |
| 11,986,274 B2 | 5/2024 | Edelman |
| 12,017,076 B2 | 6/2024 | Tan et al. |
| 12,023,476 B2 | 7/2024 | Tuval et al. |
| 12,029,891 B2 | 7/2024 | Siess et al. |
| 2001/0016686 A1 | 8/2001 | Okada et al. |
| 2001/0037093 A1 | 11/2001 | Benkowski et al. |
| 2001/0039828 A1 | 11/2001 | Shin et al. |
| 2002/0147495 A1 | 10/2002 | Petroff |
| 2002/0151761 A1 | 10/2002 | Viole et al. |
| 2003/0069465 A1 | 4/2003 | Benkowski et al. |
| 2003/0130581 A1 | 7/2003 | Salo et al. |
| 2003/0139643 A1 | 7/2003 | Smith et al. |
| 2003/0167002 A1 | 9/2003 | Nagar et al. |
| 2003/0191357 A1 | 10/2003 | Frazier |
| 2004/0022640 A1 | 2/2004 | Siess et al. |
| 2004/0044266 A1 | 3/2004 | Siess et al. |
| 2004/0065143 A1 | 4/2004 | Husher |
| 2004/0130009 A1 | 7/2004 | Tangpuz |
| 2004/0167376 A1 | 8/2004 | Peters et al. |
| 2004/0167410 A1 | 8/2004 | Hettrick |
| 2004/0225177 A1 | 11/2004 | Coleman et al. |
| 2004/0241019 A1 | 12/2004 | Goldowsky |
| 2004/0260346 A1 | 12/2004 | Overall et al. |
| 2005/0001324 A1 | 1/2005 | Dunn |
| 2005/0019167 A1 | 1/2005 | Nusser et al. |
| 2005/0107658 A1 | 5/2005 | Brockway |
| 2005/0126268 A1 | 6/2005 | Ouriev et al. |
| 2005/0267322 A1 | 12/2005 | LaRose |
| 2006/0030809 A1 | 2/2006 | Barzilay et al. |

(56) References Cited

U.S. PATENT DOCUMENTS

| | | |
|---|---|---|
| 2006/0108697 A1 | 5/2006 | Wang |
| 2006/0108901 A1 | 5/2006 | Mao-Chin et al. |
| 2006/0122583 A1 | 6/2006 | Pesach et al. |
| 2006/0196277 A1 | 9/2006 | Allen et al. |
| 2006/0229488 A1 | 10/2006 | Ayre et al. |
| 2006/0287600 A1 | 12/2006 | McEowen |
| 2006/0287604 A1 | 12/2006 | Hickey |
| 2007/0060787 A1 | 3/2007 | Peters et al. |
| 2007/0073352 A1 | 3/2007 | Euler et al. |
| 2007/0088214 A1 | 4/2007 | Shuros et al. |
| 2007/0156006 A1 | 7/2007 | Smith et al. |
| 2007/0255352 A1 | 11/2007 | Roline et al. |
| 2007/0266778 A1 | 11/2007 | Corey et al. |
| 2007/0282209 A1 | 12/2007 | Lui et al. |
| 2007/0299325 A1 | 12/2007 | Farrell et al. |
| 2008/0015517 A1 | 1/2008 | Geistert et al. |
| 2008/0082005 A1 | 4/2008 | Stern et al. |
| 2008/0091239 A1 | 4/2008 | Johansson et al. |
| 2008/0097595 A1 | 4/2008 | Gabbay |
| 2008/0102096 A1 | 5/2008 | Molin et al. |
| 2008/0108901 A1 | 5/2008 | Baba et al. |
| 2008/0108930 A1 | 5/2008 | Weitzel et al. |
| 2008/0133006 A1 | 6/2008 | Crosby et al. |
| 2008/0146996 A1 | 6/2008 | Smisson |
| 2008/0210016 A1 | 9/2008 | Zwirn et al. |
| 2008/0262289 A1 | 10/2008 | Goldowsky |
| 2008/0262361 A1 | 10/2008 | Gutfinger et al. |
| 2008/0269822 A1 | 10/2008 | Ljungstrom et al. |
| 2008/0275339 A1 | 11/2008 | Thiemann et al. |
| 2008/0306328 A1 | 12/2008 | Ercolani |
| 2009/0024042 A1 | 1/2009 | Nunez et al. |
| 2009/0025459 A1 | 1/2009 | Zhang et al. |
| 2009/0064755 A1 | 3/2009 | Fleischli et al. |
| 2009/0105799 A1 | 4/2009 | Hekmat et al. |
| 2009/0131765 A1 | 5/2009 | Roschak et al. |
| 2009/0204163 A1 | 8/2009 | Shuros et al. |
| 2009/0226328 A1 | 9/2009 | Morello |
| 2009/0312650 A1 | 12/2009 | Maile et al. |
| 2010/0010354 A1 | 1/2010 | Skerl et al. |
| 2010/0082099 A1 | 4/2010 | Vodermayer et al. |
| 2010/0087742 A1 | 4/2010 | Bishop et al. |
| 2010/0160801 A1 | 6/2010 | Takatani et al. |
| 2010/0219967 A1 | 9/2010 | Kaufmann |
| 2010/0222632 A1 | 9/2010 | Poirier |
| 2010/0222633 A1 | 9/2010 | Poirier |
| 2010/0222635 A1 | 9/2010 | Poirier |
| 2010/0222878 A1 | 9/2010 | Poirier |
| 2010/0268017 A1 | 10/2010 | Siess |
| 2010/0298625 A1 | 11/2010 | Reichenbach et al. |
| 2010/0324378 A1 | 12/2010 | Tran et al. |
| 2011/0004075 A1 | 1/2011 | Stahmann et al. |
| 2011/0022057 A1 | 1/2011 | Eigler et al. |
| 2011/0071336 A1 | 3/2011 | Yomtov |
| 2011/0144744 A1 | 6/2011 | Wampler |
| 2011/0184301 A1 | 7/2011 | Holmstrom |
| 2011/0218435 A1 | 9/2011 | Srinivasan et al. |
| 2011/0230068 A1 | 9/2011 | Pahl |
| 2012/0022645 A1 | 1/2012 | Burke |
| 2012/0084024 A1 | 4/2012 | Norcross, Jr. |
| 2012/0150089 A1 | 6/2012 | Penka et al. |
| 2012/0203476 A1 | 8/2012 | Dam |
| 2012/0247200 A1 | 10/2012 | Ahonen et al. |
| 2012/0310037 A1 | 12/2012 | Choi et al. |
| 2012/0330214 A1 | 12/2012 | Peters et al. |
| 2013/0041204 A1 | 2/2013 | Heilman et al. |
| 2013/0046129 A1 | 2/2013 | Medvedev et al. |
| 2013/0066141 A1 | 3/2013 | Doerr et al. |
| 2013/0072846 A1 | 3/2013 | Heide et al. |
| 2013/0116575 A1 | 5/2013 | Mickle et al. |
| 2013/0144379 A1 | 6/2013 | Najafi et al. |
| 2013/0289376 A1 | 10/2013 | Lang |
| 2013/0303831 A1 | 11/2013 | Evans |
| 2014/0005467 A1 | 1/2014 | Farnan et al. |
| 2014/0013852 A1 | 1/2014 | Brown et al. |
| 2014/0100414 A1 | 4/2014 | Tamez et al. |
| 2014/0114202 A1 | 4/2014 | Hein et al. |
| 2014/0128659 A1 | 5/2014 | Heuring et al. |
| 2014/0200389 A1 | 7/2014 | Yanai et al. |
| 2014/0243688 A1 | 8/2014 | Caron et al. |
| 2014/0275720 A1 | 9/2014 | Ferrari |
| 2014/0296677 A1 | 10/2014 | McEowen |
| 2014/0303426 A1 | 10/2014 | Kerkhoffs et al. |
| 2014/0342203 A1 | 11/2014 | Elian |
| 2015/0032007 A1 | 1/2015 | Ottevanger et al. |
| 2015/0141832 A1 | 5/2015 | Yu et al. |
| 2015/0141842 A1 | 5/2015 | Spanier et al. |
| 2015/0157216 A1 | 6/2015 | Stigall et al. |
| 2015/0174307 A1 | 6/2015 | Eckman et al. |
| 2015/0190092 A1 | 7/2015 | Mori |
| 2015/0250935 A1 | 9/2015 | Anderson et al. |
| 2015/0273184 A1 | 10/2015 | Scott et al. |
| 2015/0290372 A1 | 10/2015 | Muller et al. |
| 2015/0306290 A1 | 10/2015 | Rosenberg et al. |
| 2015/0306291 A1 | 10/2015 | Bonde et al. |
| 2015/0307344 A1 | 10/2015 | Ernst |
| 2015/0327921 A1 | 11/2015 | Govari |
| 2015/0335804 A1 | 11/2015 | Marseille et al. |
| 2015/0365738 A1 | 12/2015 | Purvis et al. |
| 2016/0000983 A1 | 1/2016 | Mohl et al. |
| 2016/0008531 A1 | 1/2016 | Wang et al. |
| 2016/0022889 A1 | 1/2016 | Bluvshtein et al. |
| 2016/0022890 A1 | 1/2016 | Schwammenthal et al. |
| 2016/0045165 A1 | 2/2016 | Braido et al. |
| 2016/0095968 A1 | 4/2016 | Rudser |
| 2016/0101230 A1 | 4/2016 | Ochsner et al. |
| 2016/0144166 A1 | 5/2016 | Decré et al. |
| 2016/0166747 A1 | 6/2016 | Frazier et al. |
| 2016/0213828 A1 | 7/2016 | Sievers |
| 2016/0250399 A1 | 9/2016 | Tiller et al. |
| 2016/0278856 A1 | 9/2016 | Panescu |
| 2016/0338629 A1 | 11/2016 | Doerr |
| 2017/0010144 A1 | 1/2017 | Lenner et al. |
| 2017/0021070 A1 | 1/2017 | Petersen |
| 2017/0049945 A1 | 2/2017 | Halvorsen et al. |
| 2017/0086780 A1 | 3/2017 | Sokulin et al. |
| 2017/0098491 A1 | 4/2017 | Ziaie et al. |
| 2017/0112985 A1 | 4/2017 | Yomtov |
| 2017/0128646 A1 | 5/2017 | Karch |
| 2017/0136164 A1 | 5/2017 | Yeatts |
| 2017/0202575 A1 | 7/2017 | Stanfield et al. |
| 2017/0224279 A1 | 8/2017 | Cahan et al. |
| 2017/0239407 A1 | 8/2017 | Hayward |
| 2017/0258980 A1 | 9/2017 | Katsuki et al. |
| 2017/0348470 A1 | 12/2017 | D'Ambrosio et al. |
| 2017/0354812 A1 | 12/2017 | Callaghan et al. |
| 2018/0064860 A1 | 3/2018 | Nunez et al. |
| 2018/0078159 A1 | 3/2018 | Edelman et al. |
| 2018/0093070 A1 | 4/2018 | Cottone |
| 2018/0110910 A1 | 4/2018 | Rodemerk et al. |
| 2018/0199635 A1 | 7/2018 | Longinotti-Buitoni et al. |
| 2018/0250457 A1 | 9/2018 | Morello et al. |
| 2018/0256796 A1 | 9/2018 | Hansen |
| 2018/0256800 A1 | 9/2018 | Conyers et al. |
| 2018/0264182 A1 | 9/2018 | Spanier et al. |
| 2018/0280598 A1 | 10/2018 | Curran et al. |
| 2018/0316209 A1 | 11/2018 | Gliner |
| 2018/0326131 A1 | 11/2018 | Muller et al. |
| 2018/0353667 A1 | 12/2018 | Moyer et al. |
| 2018/0369469 A1 | 12/2018 | Le Duc De Lillers et al. |
| 2019/0001038 A1 | 1/2019 | Yomtov et al. |
| 2019/0054223 A1 | 2/2019 | Frazier et al. |
| 2019/0083690 A1 | 3/2019 | Siess et al. |
| 2019/0192752 A1 | 6/2019 | Tiller et al. |
| 2019/0192753 A1 | 6/2019 | Liu et al. |
| 2019/0209755 A1 | 7/2019 | Nix et al. |
| 2019/0209758 A1 | 7/2019 | Tuval et al. |
| 2019/0216995 A1 | 7/2019 | Kapur et al. |
| 2019/0217002 A1 | 7/2019 | Urakabe |
| 2019/0223877 A1 | 7/2019 | Nitzen et al. |
| 2019/0240680 A1 | 8/2019 | Hayakawa |
| 2019/0254543 A1 | 8/2019 | Hartholt et al. |
| 2019/0282741 A1 | 9/2019 | Franano et al. |
| 2019/0282744 A1 | 9/2019 | D'Ambrosio et al. |
| 2019/0351117 A1 | 11/2019 | Cambronne et al. |

(56) References Cited

U.S. PATENT DOCUMENTS

| | | |
|---|---|---|
| 2019/0351118 A1 | 11/2019 | Graichen et al. |
| 2020/0016309 A1 | 1/2020 | Kallenbach et al. |
| 2020/0038567 A1 | 2/2020 | Siess et al. |
| 2020/0060559 A1 | 2/2020 | Edelman et al. |
| 2020/0069857 A1 | 3/2020 | Schwammenthal et al. |
| 2020/0147283 A1 | 5/2020 | Tanner et al. |
| 2020/0164125 A1 | 5/2020 | Muller et al. |
| 2020/0164126 A1 | 5/2020 | Muller |
| 2020/0253583 A1 | 8/2020 | Brisken et al. |
| 2020/0312450 A1 | 10/2020 | Agnello et al. |
| 2021/0268264 A1 | 9/2021 | Stotz |
| 2021/0290087 A1 | 9/2021 | Schlebusch |
| 2021/0290930 A1 | 9/2021 | Kasel |
| 2021/0290933 A1 | 9/2021 | Stotz |
| 2021/0339002 A1 | 11/2021 | Schlebusch et al. |
| 2021/0339004 A1 | 11/2021 | Schlebusch et al. |
| 2021/0346674 A1 | 11/2021 | Baumbach et al. |
| 2021/0346675 A1 | 11/2021 | Schlebusch et al. |
| 2021/0346677 A1 | 11/2021 | Baumbach et al. |
| 2021/0346678 A1 | 11/2021 | Baumbach et al. |
| 2021/0378523 A1 | 12/2021 | Budde |
| 2021/0379359 A1 | 12/2021 | Schellenberg |
| 2021/0379360 A1 | 12/2021 | Schellenberg |
| 2021/0393944 A1 | 12/2021 | Wenning |
| 2022/0016411 A1 | 1/2022 | Winterwerber |
| 2022/0032032 A1 | 2/2022 | Schlebusch et al. |
| 2022/0032036 A1 | 2/2022 | Baumbach et al. |
| 2022/0039669 A1 | 2/2022 | Schlebusch et al. |
| 2022/0047173 A1 | 2/2022 | Stotz et al. |
| 2022/0050037 A1 | 2/2022 | Stotz et al. |
| 2022/0072298 A1 | 3/2022 | Spanier et al. |
| 2022/0076807 A1 | 3/2022 | Agnello |
| 2022/0079457 A1 | 3/2022 | Tuval et al. |
| 2022/0105339 A1 | 4/2022 | Nix et al. |
| 2022/0126085 A1 | 4/2022 | Farnan |
| 2022/0126086 A1 | 4/2022 | Schlebusch et al. |
| 2022/0142462 A1 | 5/2022 | Douk et al. |
| 2022/0161019 A1 | 5/2022 | Mitze et al. |
| 2023/0173250 A1 | 6/2023 | Stigloher |
| 2023/0191141 A1 | 6/2023 | Wenning et al. |
| 2024/0011808 A1 | 1/2024 | Winzer et al. |
| 2024/0074828 A1 | 3/2024 | Wenning |
| 2024/0245902 A1 | 7/2024 | Schlebusch et al. |

FOREIGN PATENT DOCUMENTS

| | | |
|---|---|---|
| CN | 1222862 A | 7/1999 |
| CN | 1202871 C | 5/2005 |
| CN | 1661338 A | 8/2005 |
| CN | 101128168 | 2/2008 |
| CN | 101208045 | 6/2008 |
| CN | 101214158 | 7/2008 |
| CN | 101351237 | 1/2009 |
| CN | 101448535 | 6/2009 |
| CN | 101460094 | 6/2009 |
| CN | 101579233 | 11/2009 |
| CN | 201437016 | 4/2010 |
| CN | 101711683 | 5/2010 |
| CN | 201658687 | 12/2010 |
| CN | 102421372 | 4/2012 |
| CN | 102803923 | 11/2012 |
| CN | 103328018 | 9/2013 |
| CN | 103857326 | 6/2014 |
| CN | 103957957 | 7/2014 |
| CN | 104105449 | 10/2014 |
| CN | 104188687 | 12/2014 |
| CN | 106104229 | 11/2016 |
| CN | 106333707 | 1/2017 |
| CN | 206007680 | 3/2017 |
| CN | 107530479 | 1/2018 |
| CN | 107632167 | 1/2018 |
| CN | 109939282 | 6/2019 |
| CN | 209790495 | 12/2019 |
| CN | 210020563 | 2/2020 |
| DE | 195 20 920 | 12/1995 |
| DE | 198 21 307 | 10/1999 |
| DE | 100 59 714 | 5/2002 |
| DE | 100 60 275 | 6/2002 |
| DE | 101 44 269 | 3/2003 |
| DE | 102 26 305 | 10/2003 |
| DE | 10 2006 001 180 | 9/2007 |
| DE | 10 2009 007 216 | 8/2010 |
| DE | 10 2009 011 726 | 9/2010 |
| DE | 10 2009 025 464 | 1/2011 |
| DE | 10 2009 047 845 | 3/2011 |
| DE | 10 2011 106 142 | 12/2012 |
| DE | 20 2011 110 389 | 9/2013 |
| DE | 10 2015 004 177 | 10/2015 |
| DE | 10 2015 219 263 | 4/2017 |
| DE | 10 2015 222 199 | 5/2017 |
| DE | 20 2015 009 422 | 7/2017 |
| DE | 10 2012 207 042 | 9/2017 |
| DE | 10 2016 013 334 | 4/2018 |
| DE | 10 2018 208 536 | 12/2019 |
| DE | 10 2018 208 862 | 12/2019 |
| DE | 10 2018 208 916 | 12/2019 |
| DE | 10 2018 208 927 | 12/2019 |
| DE | 10 2018 208 945 | 12/2019 |
| DE | 10 2018 210 076 | 12/2019 |
| DE | 10 2018 212 153 | 1/2020 |
| DE | 10 2018 213 151 | 2/2020 |
| DE | 10 2018 213 350 | 2/2020 |
| DE | 10 2018 220 658 | 6/2020 |
| DE | 10 2018 222 505 | 6/2020 |
| DE | 10 2020 102 473 | 8/2021 |
| DE | 11 2020 003 151 | 3/2022 |
| EP | 0 794 411 | 9/1997 |
| EP | 0 916 359 | 5/1999 |
| EP | 1 062 959 | 12/2000 |
| EP | 1 339 443 | 11/2001 |
| EP | 1 011 803 | 9/2004 |
| EP | 1 354 606 | 6/2006 |
| EP | 2 143 385 | 1/2010 |
| EP | 2 175 770 | 4/2010 |
| EP | 2 187 807 | 6/2012 |
| EP | 2 570 143 | 3/2013 |
| EP | 2 401 003 | 10/2013 |
| EP | 1 871 441 | 11/2014 |
| EP | 2 859 911 | 4/2015 |
| EP | 2 213 227 | 8/2016 |
| EP | 2 835 141 | 8/2016 |
| EP | 3 088 016 | 11/2016 |
| EP | 2 585 129 | 3/2017 |
| EP | 2 945 661 | 11/2017 |
| EP | 2 136 861 | 12/2017 |
| EP | 3 020 426 | 12/2017 |
| EP | 3 287 154 | 2/2018 |
| EP | 3 205 359 | 8/2018 |
| EP | 3 205 360 | 8/2018 |
| EP | 3 389 738 | 8/2019 |
| EP | 2 505 090 | 12/2019 |
| EP | 3 668 560 | 6/2020 |
| EP | 3 720 520 | 10/2020 |
| EP | 3 753 594 | 12/2020 |
| EP | 3 357 523 | 1/2021 |
| EP | 3 490 628 | 2/2021 |
| EP | 3 487 548 | 3/2021 |
| EP | 3 509 661 | 3/2021 |
| EP | 3 515 523 | 3/2021 |
| EP | 3 528 863 | 3/2021 |
| EP | 3 615 103 | 3/2021 |
| EP | 4 271 461 | 3/2021 |
| EP | 3 131 600 | 6/2021 |
| EP | 3 131 615 | 6/2021 |
| EP | 3 463 505 | 9/2021 |
| EP | 3 884 970 | 9/2021 |
| EP | 2 599 510 | 10/2021 |
| EP | 3 003 421 | 10/2021 |
| EP | 3 027 241 | 10/2021 |
| EP | 3 668 561 | 10/2021 |
| EP | 3 164 168 | 12/2021 |
| EP | 3 344 129 | 12/2021 |
| EP | 3 624 867 | 3/2022 |
| EP | 3 651 822 | 3/2022 |

(56) References Cited

FOREIGN PATENT DOCUMENTS

| | | |
|---|---|---|
| EP | 3 689 389 | 3/2022 |
| EP | 3 737 436 | 3/2022 |
| EP | 3 984 589 | 4/2022 |
| EP | 3 654 006 | 5/2022 |
| EP | 3 737 310 | 7/2022 |
| EP | 2 999 400 | 8/2022 |
| EP | 3 711 788 | 8/2022 |
| EP | 3 694 573 | 9/2022 |
| EP | 3 600 477 | 10/2022 |
| EP | 3 897 768 | 10/2022 |
| EP | 2 892 583 | 1/2023 |
| EP | 3 370 797 | 1/2023 |
| EP | 3 597 231 | 1/2023 |
| EP | 3 668 562 | 1/2023 |
| EP | 3 856 275 | 1/2023 |
| EP | 3 003 420 | 2/2023 |
| EP | 3 397 299 | 2/2023 |
| EP | 3 046 594 | 3/2023 |
| EP | 3 938 005 | 4/2023 |
| EP | 3 685 562 | 5/2023 |
| EP | 3 397 298 | 7/2023 |
| EP | 3 809 959 | 7/2023 |
| EP | 2 072 150 | 9/2023 |
| EP | 2 961 984 | 9/2023 |
| EP | 3 352 808 | 9/2023 |
| EP | 3 768 156 | 9/2023 |
| EP | 4 052 754 | 10/2023 |
| EP | 3 157 596 | 11/2023 |
| EP | 3 766 428 | 11/2023 |
| EP | 3 781 027 | 11/2023 |
| EP | 4 061 470 | 11/2023 |
| EP | 4 070 720 | 11/2023 |
| EP | 3 449 958 | 12/2023 |
| EP | 3 687 596 | 12/2023 |
| EP | 3 768 340 | 12/2023 |
| EP | 3 801 675 | 1/2024 |
| EP | 3 566 636 | 2/2024 |
| EP | 3 634 526 | 2/2024 |
| EP | 3 768 347 | 2/2024 |
| EP | 3 790 606 | 2/2024 |
| EP | 3 930 780 | 2/2024 |
| EP | 3 397 147 | 3/2024 |
| EP | 3 782 695 | 3/2024 |
| EP | 3 854 448 | 3/2024 |
| EP | 4 140 532 | 5/2024 |
| EP | 3 693 038 | 6/2024 |
| EP | 3 970 765 | 7/2024 |
| ES | 2 913 485 | 6/2022 |
| JP | S59-080229 | 5/1984 |
| JP | S61-125329 | 6/1986 |
| JP | S62-113555 | 7/1987 |
| JP | S62-204733 | 9/1987 |
| JP | S62-282284 | 12/1987 |
| JP | S64-68236 | 3/1989 |
| JP | H02-055886 | 2/1990 |
| JP | H02-234750 | 9/1990 |
| JP | H05-079875 | 3/1993 |
| JP | H06-218044 | 8/1994 |
| JP | H07-047025 | 5/1995 |
| JP | H08-057042 | 3/1996 |
| JP | H08-066398 | 3/1996 |
| JP | H08-327527 | 12/1996 |
| JP | H10-052489 | 2/1998 |
| JP | H10-505766 | 6/1998 |
| JP | H11-239617 | 9/1999 |
| JP | 2000-512191 | 9/2000 |
| JP | 2001-037728 | 2/2001 |
| JP | 2001-506140 | 5/2001 |
| JP | 2001-276213 | 10/2001 |
| JP | 2002-525175 | 8/2002 |
| JP | 2003-019197 | 1/2003 |
| JP | 2003-047656 | 2/2003 |
| JP | 2003-062065 | 3/2003 |
| JP | 2004-515278 | 5/2004 |
| JP | 2005-028137 | 2/2005 |
| JP | 2005-192687 | 7/2005 |
| JP | 2006-528006 | 12/2006 |
| JP | 2007-222644 | 9/2007 |
| JP | 2008-511414 | 4/2008 |
| JP | 2006-518249 | 8/2008 |
| JP | 2008-178690 | 8/2008 |
| JP | 2009-504290 | 2/2009 |
| JP | 2009-240348 | 10/2009 |
| JP | 2010-518907 | 6/2010 |
| JP | 2012-520157 | 9/2012 |
| JP | 2013-128792 | 7/2013 |
| JP | 2014-524274 | 9/2014 |
| JP | 2015-514529 | 5/2015 |
| JP | 2015-514531 | 5/2015 |
| JP | 2015-515429 | 5/2015 |
| JP | 2015-122448 | 7/2015 |
| JP | 2015-527172 | 9/2015 |
| JP | 2015-181800 | 10/2015 |
| JP | 2016-002466 | 1/2016 |
| JP | 2016-509950 | 4/2016 |
| JP | 2017-500932 | 1/2017 |
| JP | 2017-176719 | 10/2017 |
| JP | 2017-532084 | 11/2017 |
| JP | 2019-523110 | 8/2019 |
| JP | 2020-072985 | 5/2020 |
| WO | WO 92/015239 | 9/1992 |
| WO | WO 98/043688 | 10/1998 |
| WO | WO 00/033047 | 6/2000 |
| WO | WO 2006/122001 | 11/2006 |
| WO | WO 2010/142286 | 12/2010 |
| WO | WO 2010/143272 | 12/2010 |
| WO | WO 2012/018917 | 2/2012 |
| WO | WO 2012/112378 | 8/2012 |
| WO | WO 2013/160443 | 10/2013 |
| WO | WO 2014/042925 | 3/2014 |
| WO | WO 2014/141284 | 9/2014 |
| WO | WO 2014/165635 | 10/2014 |
| WO | WO 2015/085220 | 6/2015 |
| WO | WO 2016/001284 | 1/2016 |
| WO | WO 2016/066180 | 5/2016 |
| WO | WO 2016/137743 | 9/2016 |
| WO | WO 2017/032751 | 3/2017 |
| WO | WO 2017/066257 | 4/2017 |
| WO | WO 2017/106190 | 6/2017 |
| WO | WO 2017/147291 | 8/2017 |
| WO | WO 2017/214118 | 12/2017 |
| WO | WO 2018/048800 | 3/2018 |
| WO | WO 2018/109038 | 6/2018 |
| WO | WO 2018/213089 | 11/2018 |
| WO | WO 2019/013794 | 1/2019 |
| WO | WO 2019/034670 | 2/2019 |
| WO | WO 2019/034775 | 2/2019 |
| WO | WO 2019/078723 | 4/2019 |
| WO | WO 2019/126721 | 6/2019 |
| WO | WO 2019/137911 | 7/2019 |
| WO | WO 2019/193604 | 10/2019 |
| WO | WO 2019/219883 | 11/2019 |
| WO | WO 2019/229210 | 12/2019 |
| WO | WO 2019/229220 | 12/2019 |
| WO | WO 2019/234145 | 12/2019 |
| WO | WO 2019/234146 | 12/2019 |
| WO | WO 2019/234148 | 12/2019 |
| WO | WO 2019/234149 | 12/2019 |
| WO | WO 2019/234151 | 12/2019 |
| WO | WO 2019/234152 | 12/2019 |
| WO | WO 2019/234153 | 12/2019 |
| WO | WO 2019/234161 | 12/2019 |
| WO | WO 2019/234162 | 12/2019 |
| WO | WO 2019/234163 | 12/2019 |
| WO | WO 2019/234164 | 12/2019 |
| WO | WO 2019/234166 | 12/2019 |
| WO | WO 2019/234167 | 12/2019 |
| WO | WO 2019/234169 | 12/2019 |
| WO | WO 2019/243582 | 12/2019 |
| WO | WO 2020/030686 | 2/2020 |
| WO | WO 2020/030706 | 2/2020 |
| WO | WO 2020/064707 | 4/2020 |
| WO | WO 2020/089429 | 5/2020 |
| WO | WO 2020/198280 | 10/2020 |

(56) References Cited

FOREIGN PATENT DOCUMENTS

| WO | WO 2020/243756 | 12/2020 |
| WO | WO 2022/074136 | 4/2022 |
| WO | WO 2022/109590 | 5/2022 |
| WO | WO 2022/173970 | 8/2022 |
| WO | WO 2023/049813 | 3/2023 |

OTHER PUBLICATIONS

Leguy et al., "Assessment of Blood Volume Flow in Slightly Curved Arteries from a Single Velocity Profile", Journal of Biomechanics, 2009, pp. 1664-1672.

Sinha et al., "Effect of Mechanical Assistance of the Systemic Ventricle in Single Ventricle Circulation with Cavopulmonary Connection", The Journal of Throacic and Cardiovascular Surgery, Apr. 2014, vol. 147, No. 4, pp. 1271-1275.

"Understanding Hot-Wire Anemometry", Advanced Thermal Solutions, Inc., 2007, pp. 13-17.

Vieli, A., "Doppler Flow Determination", BJA: British Journal of Anaesthesia, 1988, vol. 60, pp. 107S-112S.

Yuanyuan et al., "Characteristics Analysis for Doppler Ultrasound Blood Flow Signals", China Medical Device Information, 5(1), Feb. 28, 1999, pp. 36-42.

Zhang, Dabiao et al., "Design of Microwave Velocity and Distance Monitor System", Instrument Technique and Sensor, Hebei Normal University, Apr. 25, 2004, pp. 3.

Vollkron et al., "Advanced Suction Detection for an Axial Flow Pump", Artificial Organs, 2006, vol. 30, No. 9, pp. 665-670.

Vollkron et al., "Development of a Suction Detection System for Axial Blood Pumps", Artificial Organs, 2004, vol. 28, No. 8, pp. 709-716.

Lombardi et al., "Flow Rate Profiler: an instrument to measure blood velocity profiles", Ultrasonics, 2001, vol. 39, pp. 143-150.

Mushi et al., "Identification of Fluidic Element Models to Simulate the Short-Term Baroreflex", Proceedings of the 45th IEEE Conference on Decision & Control, San Diego, CA, Dec. 13-15, 2006, pp. 6.

Hertz Ph. D et al., "Ultrasonic Engineering in Heart Diagnosis", The American Journal of Cardiology, Jan. 1967, vol. 19, No. 1, pp. 6-17.

International Preliminary Report on Patentability and Written Opinion received in PCT Application No. PCT/EP2019/064804, dated May 13, 2020 in 12 pages.

International Search Report and Written Opinion received in PCT Application No. PCT/EP2019/064804, dated Sep. 9, 2019 in 14 pages.

Kong et al., "A Stein Equation Approach for Solutions to the Diophantine Equations," 2010 Chinese Control and Decision Conference, Xuzhou, May 26, 2010, pp. 3024-3028.

Koseli et al., "Online Viscosity Measurement of Complex Solutions Using Ultrasound Doppler Velocimetry", Turk J Chem, Jan. 2006, vol. 30, pp. 297-305.

McCormick et al., "Resolution of a 2/spl pi/ Ambiguity Problem in Multiple Frequency Spectral Estimation," in IEEE Transactions on Aerospace and Electronic Systems, Jan. 1995, vol. 31, No. 1, pp. 2-8.

Syrmos et al., "A Generalized Bezout Equation in Output Feedback Design," Proceedings of the 31st IEEE Conference on Decision and Control, Tucson, AZ, USA, Dec. 1992, vol. 4, pp. 3590-3594.

Udesen et al., "A Simple Method to Reduce Aliasing Artifacts in Color Flow Mode Imaging", IEEE Ultrasonics Symposium, 2005, Rotterdam, The Netherlands, Sep. 18-21, 2005, pp. 1352-1355.

Murali, Akila, "Design of Inductive Coils for Wireless Power Transfer to Pediatric Implants", A graduate project submitted in partial fulfillment of the requirements for the degree of Master of Science in Electrical Engineering, California State University, Northridge, May 2018, pp. 37.

METHOD FOR DETERMINING A FLOW RATE OF A FLUID FLOWING THROUGH AN IMPLANTED VASCULAR SUPPORT SYSTEM, AND IMPLANTABLE VASCULAR SUPPORT SYSTEM

BACKGROUND

Field

The invention relates to a method for determining a flow rate of a fluid flowing through an implantable vascular assist system, an implantable vascular assist system, and the use of pulsed Doppler measurements at different pulse repetition rates. The invention is used, in particular, in (fully) implanted left ventricular assist systems (LVAD).

Description of Related Art

It is known to integrate ultrasonic volume flow sensors in ventricular assist systems in order to find the so-called pump volume flow, which quantifies the fluid volume flow through the assist system itself, with said ultrasonic volume flow sensors. In this case, the ultrasonic volume flow sensors can carry out pulsed Doppler measurements or the pulsed wave Doppler (PWD) method. This method requires only one ultrasonic transducer element and makes it possible to select with a high degree of accuracy the distance of the observation window from the ultrasonic element. In the PWD systems known from the prior art, ultrasonic pulses are emitted at a defined pulse repetition rate (PRF). In this case, the pulse repetition rate must exceed double the maximum occurring Doppler frequency shift in order not to violate the Nyquist theorem. If this condition is not fulfilled, aliasing will occur; that is to say, ambiguities will occur in the detected frequency spectrum.

As a result of the geometric design of the measurement setup in ventricular assist systems (VADs), it may be that the range of measurement or the observation window is so far away from the ultrasonic transducer that the signal transit time of the ultrasonic pulse from the transducer to the range of measurement and back to the transducer cannot be disregarded. Because, in the PWD method, a new ultrasonic pulse may not or rather should not be emitted (at least in theory) until the preceding ultrasonic pulse no long sends any significant echoes, the signal transit time limits the maximum possible pulse repetition rate. At the typically high flow rates, prevailing in ventricular assist systems, and under the geometric boundary conditions for the distance of the observation window from the ultrasonic element, the Nyquist sampling theorem will be inevitably violated, with the result that ambiguities (aliasing) will occur in the spectrum.

Ventricular assist systems with ultrasonic sensors not using the PWD method are usually equipped with two ultrasonic transducers. Although it is possible for the transit time problem described above to occur, this problem can be solved in a different way once these systems are properly implemented. However, ventricular assist systems with ultrasonic sensors using the PWD method are particularly susceptible to the described effect at medium to high flow rates. At the present time, the state of the art requires that the fixed pulse repetition rate be selected in such a way that aliasing does not occur.

SUMMARY

The object of the present invention is to provide an improved method for determining a flow rate of a fluid flowing through an implanted vascular assist system and to provide an improved implanted vascular assist system, in which the flow rate of a fluid flowing through said system can be determined.

In particular, the object of the present invention is to provide a method for determining a flow rate of a fluid and an improved implantable vascular assist system, in which the process of determining the flow rate of a fluid flowing through said system is provided, in which process it is possible to use only one ultrasonic transducer to determine the flow rate at the flow rates prevailing in a ventricular assist system, even in the case of a large signal transit time of an ultrasonic pulse from the ultrasonic transducer to the range of measurement and back.

This object is achieved by means of the method disclosed in and the implantable vascular assist system disclosed herein.

Advantageous embodiments of the invention are disclosed in the dependent claims.

The present invention includes a method for determining a flow rate of a fluid flowing through an implanted vascular assist system, said method comprising the following steps:
a) carrying out a first pulsed Doppler measurement at a first pulse repetition rate by means of an ultrasonic sensor of the assist system,
b) carrying out a second pulsed Doppler measurement at a second pulse repetition rate by means of the ultrasonic sensor of the assist system, wherein the second pulse repetition rate is different from the first pulse repetition rate,
c) determining the flow rate using the measurement results of the first pulsed Doppler measurement and the second pulsed Doppler measurement.

The vascular assist system is preferably a cardiac assist system, particularly preferably a ventricular assist system. The assist system is usually used to help convey the blood in the cardiovascular system of a human being and, if applicable, patients. The assist system can be arranged at least partially in a blood vessel. The blood vessel is, for example, the aorta, in particular in the case of a left ventricular assist system; or the blood vessel is the common trunk (Truncus pulmonalis) that is divided into the two pulmonary arteries, in particular in the case of a right ventricular assist system. The assist system is preferably arranged at the outlet of the left ventricle of the heart or the left chamber of the heart. It is particularly preferable for the assist system to be arranged in the position of the aortic valve.

The solution proposed herein helps, in particular, to compensate for the aliasing effects in a medical pulsed wave Doppler system. The method can help to determine the fluid flow rate and/or a fluid volume flow from a ventricle of a heart, in particular from a (left) ventricle of a heart to the aorta in the region of a (fully) implanted (left) ventricular assist system. As a rule, the fluid is blood. The flow rate is determined in a fluid flow or the fluid volume flow that flows through the assist system, in particular through a (inlet) cannula of the assist system. The method allows the flow rate and/or the fluid volume flow of the blood flow to be determined in an advantageous way with high quality even outside the surgery scenario, in particular by means of the implanted assist system itself.

In the solution proposed here, a correlation between the measured (main) peak in the Doppler frequency spectrum and the applied pulse repetition rate (PRF) can be used in a particularly advantageous manner. If a measurement is carried out several times at different PRFs, then the best possible maxima of the respective measurement cycle with modified PRF are located at a different position in the frequency spectrum. As a result, a system of equations can be set up in an advantageous way by varying the PRF values, and said system of equations can be used to eliminate the ambiguities and to find unique solutions. This aspect makes it possible to calculate in a particularly advantageous manner the main rate component of a blood flow despite a so-called "spectrum wrapping" or despite aliasing.

In step a), a first pulsed Doppler measurement is carried out at a first pulse repetition rate (first PRF or $PRF_1$) by means of an ultrasonic sensor of the assist system. In particular, the pulsed wave Doppler (PWD) method is used to carry out the pulsed Doppler measurement. In particular, a first PWD measurement cycle is run in step a).

In step b), a second pulsed Doppler measurement is carried out at a second pulse repetition rate (second PRF or $PRF_2$) by means of the ultrasonic sensor of the assist system. In this case, the second pulse repetition rate differs from the first pulse repetition rate. For example, the second pulse repetition rate is greater than or less than the first pulse repetition rate. In other words, this means in particular that the first pulse repetition rate and the second pulse repetition rate are pulse repetition rates that are different from one another. In particular, a second PWD measurement cycle is run in step b). In addition, a repetition of a PWD measurement cycle with different fixed PRF values, for example, 20 KHz and 25 kHz, is preferably carried out in steps a) and b).

Other (pulsed) Doppler measurements, for example a third, fourth, and/or fifth Doppler measurement, can also be carried out. For these measurements, the situations listed in conjunction with the first and second pulsed Doppler measurement may apply correspondingly. In particular, all of these pulsed Doppler measurements have pulse repetition rates that are different from one another. If other Doppler measurements are carried out, they can be included (as needed) in the determination process in step c). In other words, this means in particular that the process of determining the flow rate can also be carried out using the measurement results of the first pulsed Doppler measurement, the second pulsed Doppler measurement, and other pulsed Doppler measurements (insofar as they are available). However, the number of Doppler measurements is preferably just large enough that a unique flow rate can be determined by means of the method, an aspect that can be achieved here in a particularly advantageous manner with two Doppler measurements.

A PWD measurement cycle comprises, in particular, a sequence of a (defined) number of successively emitted ultrasonic pulses. The Doppler measurements that are carried out at different PRFs in steps a) and b) are basically carried out with respect to the same fluid flow, for example in the same observation window or in the same range of measurement. In other words, this means in particular that the first pulsed Doppler measurement and the second pulsed Doppler measurement take place within the same observation window or range of measurement. In addition, it is advantageous for the two pulsed Doppler measurements to follow one another immediately in terms of time or for there to be no significant time interval between the two measurements.

In step c), the flow rate is determined using the measurement results of the first pulsed Doppler measurement and the second pulsed Doppler measurement. As a rule, the measurement results are ambiguous. This ambiguity can be explained, in particular, by the fact that there is generally a violation of the Nyquist sampling theorem here. This violation of the Nyquist sampling theorem is caused, in particular, by the fact that there are comparatively long signal transit times between the ultrasonic sensor and the observation window or the range of measurement in the assist system and, in the case of the pulsed Doppler measurements, a new ultrasonic pulse is usually not emitted until an echo of a just previously emitted ultrasonic pulse has been received.

The flow rate can be determined, for example, in such a way that initially a first Doppler frequency spectrum is detected on the basis of the first pulsed Doppler measurement and a second Doppler frequency spectrum is detected on the basis of the second pulsed Doppler measurement. In other words, this means in particular that, initially, a calculation of the (respective) Doppler frequency spectrum is carried out for each PRF measurement. For example, a first main frequency component of the first Doppler frequency spectrum and a second main frequency component of the second Doppler frequency spectrum can also be determined. In other words, this means in particular that a determination of the main frequency component of the (respective) Doppler spectrum (for example, single frequency peak or a so-called "template matching" of the expected frequency distribution) takes place.

A system of equations can be set up by way of example on the basis of the first main frequency component and the second main frequency component. The system of equations can be solved, for example, by setting and solving the resulting linear Diophantine equation (for example, solvable by Bezout coefficients). The actual or unique Doppler frequency can be determined from this solution. This (unique) Doppler frequency can be used to calculate the flow rate in the usual manner.

In accordance with one advantageous embodiment, it is proposed that at least in one of the two steps a) and b), a new ultrasonic pulse is emitted only after an echo of a just previously emitted ultrasonic pulse has been received. In both steps a) and b), a new ultrasonic pulse is emitted preferably only after an echo of a just previously emitted ultrasonic pulse has been received. Preferably, a new ultrasonic pulse is not emitted until all (significant) echoes of a just previously emitted ultrasonic pulse have been received.

In accordance with one advantageous embodiment, it is proposed that a maximum pulse repetition rate of the pulsed Doppler measurements may be smaller and/or smaller than twice a maximum occurring Doppler shift. The maximum pulse repetition rate of the pulsed Doppler measurements is preferably smaller than the maximum occurring or the expected Doppler shift. If the maximum pulse repetition rate is less than twice the maximum occurring Doppler shift, then, in principle, the Nyquist sampling theorem will inevitably be violated. However, this violation may be necessary in order to be able to carry out a PWD method in a vascular assist system.

In accordance with one advantageous embodiment, it is proposed that a correlation between a detected main frequency component of the Doppler frequency spectrum (in particular, peak in the Doppler contribution to the frequency spectrum) of a pulsed Doppler measurement and the pulse repetition rate applied for this Doppler measurement be used in step c). The main frequency component of the (respective) Doppler frequency spectrum is basically the frequency component that is characteristic of the measured flow rate. The main frequency component is, in particular, a (local) maximum, a (local) amplitude, or a (secondary) peak in the Doppler frequency spectrum ("in the Doppler frequency spectrum" is here, in particular, a short form for "in the Doppler contribution to the frequency spectrum"; this is meant to clarify that the peak does not mean the (ever larger) carrier line in the spectrum). A correlation between a detected peak in the Doppler frequency spectrum of a pulsed Doppler measurement and the pulse repetition rate applied for this Doppler measurement is preferably used in step c). Furthermore, the first and the second pulsed Doppler measurement cycle are preferably used or set up in each case for this correlation.

In accordance with one advantageous embodiment, it is proposed that a linear equation system be solved in step c), where a Doppler shift is shown as a function of main frequency components of the first pulsed Doppler measurement and the second pulsed Doppler measurement. The Doppler shift can also be referred to as a Doppler frequency (formula symbol df or $\Delta f$). In the linear equation system, the Doppler shift is used preferably as a function of the main frequency components and the (different) pulse repetition rates of the first pulsed Doppler measurement and the second pulsed Doppler measurement. The number of equations in the equation system generally corresponds to the number of Doppler measurements that have been carried out. The linear equation system preferably comprises, in particular, two linear equations. In this case, the first linear equation preferably gives the Doppler shift as a function of the main frequency component of the first Doppler frequency spectrum and/or the first pulse repetition rate. The second linear equation preferably gives the Doppler shift as a function of the main frequency component of the second Doppler frequency spectrum and/or the second pulse repetition rate.

In accordance with an additional advantageous embodiment, it is proposed that a linear Diophantine equation be set up on the basis of the linear equation system. A linear Diophantine equation is an equation of the form $a_1 x_1 + a_2 x_2 + a_3 x_3 + \ldots + a_n x_n + c = 0$ with integer coefficients ai, where, in this case in particular the solutions of interest are the integer ones. Linear means that the variables $x_i$ do not occur in powers greater than one. The linear Diophantine equation can be set up, for example, in such a way that the two linear equations are resolved after the Doppler shift and are subsequently equated.

In accordance with another advantageous embodiment, it is proposed that the linear Diophantine equation be solved using Bezout coefficients or a method of exhaustion. The so-called Bezout coefficients can be determined, in particular, by solving the equation $n_1 \cdot PRF_1 + n_2 \cdot PRF_2 = ggT(PRF_1, PRF_2)$. Said equation shows, in particular, that the largest common divisor ggT of two integer numbers, for example $PRF_1$ and $PRF_2$, can be shown as a linear combination of the integer coefficients $n_1$ and $n_2$. The Bezout coefficients determined in this way are used, in particular, to solve the Diophantine equation that has been set up. The method of exhaustion can also be referred to as a so-called "brute force" method. This method describes a solution method that is based on trying all possible (or at least many possible) cases.

In accordance with one advantageous embodiment, it is proposed that the flow rate be used to determine a fluid volume flow through the assist system. In other words, said fluid volume flow relates in particular to the fluid volume flow of a fluid that flows (only) through the assist system itself, for example through an (inlet) cannula of the assist system. This fluid volume flow is usually the so-called pump volume flow ($Q_p$), which quantifies only the flow through the assist system itself. If this value is known in addition to the total volume flow or the heart-time volume ($Q_{HTV}$), then the so-called assist level can be calculated from the ratio of $Q_p$ to $Q_{HTV}$ (i.e., $Q_P/Q_{HTV}$). In order to determine the fluid volume flow, the determined flow rate can be multiplied, for example by a cross section of the assist system through which cross section the fluid can flow, in particular a cross section of a cannula through which cross section the fluid can flow.

In accordance with a further aspect, an implantable vascular assist system is proposed, comprising:
an ultrasonic sensor designed to carry out pulsed Doppler measurements at different pulse repetition rates,
a processing unit designed to determine a flow rate of a fluid flowing through the assist system, using the measurement results of the pulsed Doppler measurements at different pulse repetition rates.

The assist system is preferably a left ventricular assist system (LVAD) or a percutaneous, minimally invasive left heart assist system. Furthermore, it is preferably fully implantable. In other words, this means in particular that the means required for detection, in particular the ultrasonic sensor, are located completely in the body of the patient and remain there. The assist system can also be constructed of multiple parts or a plurality of components that can be arranged at a distance from one another, so that, for example, the ultrasonic sensor and the processing unit (measurement unit) can be arranged so as to be separated from one another by means of a cable. In the multipart embodiment, the processing unit, which is arranged separately from the ultrasonic sensor, can also be implanted or even arranged outside the body of the patient. In any case, it is not absolutely necessary for the processing unit to also be arranged in the body of the patient. For example, the assist system can be implanted in such a way that the processing unit is arranged on the skin of the patient or outside the body of the patient and a connection to the ultrasonic sensor arranged in the body is established. The assist system is particularly preferably designed or lends itself in such a way that it can be arranged at least partially in one ventricle, preferably the left ventricle of a heart and/or an aorta, in particular in the aortic valve position.

Furthermore, the assist system preferably comprises a cannula, in particular an inlet cannula, a continuous flow machine, for example a pump, and/or an electric motor. In this case, the electric motor is usually a component of the continuous flow machine. The (inlet) cannula is preferably designed in such a way that in the implanted state it can guide fluid out of a (left) ventricle of a heart to the continuous flow machine. The assist system preferably is formed in an elongated and/or tubular manner. The cannula and the continuous flow machine are arranged in the region of the opposite ends of the assist system.

In particular, exactly and only one ultrasonic sensor is provided. The ultrasonic sensor has preferably exactly and only one ultrasonic transducer element. This is sufficient for a Doppler measurement, especially if the PWD method is used.

The assist system is advantageously designed to carry out a method proposed herein.

In accordance with another aspect, it is proposed that pulsed Doppler measurements at different pulse repetition rates be used to correct an ambiguous measurement result of an ultrasonic sensor of an implanted vascular assist system. Preferably, at least one method proposed herein or an assist system proposed herein is used to correct an ambiguous measurement result of the ultrasonic sensor.

The details, features, and advantageous embodiments explained in conjunction with the method can also appear correspondingly in the assist system presented herein and/or in the use thereof and vice versa. To this extent, reference is made in full to said explanations in order to characterize the features in more precise detail.

BRIEF DESCRIPTION OF THE FIGURES

The solution presented herein and the technical environment thereof are explained in greater detail below with reference to the figures. It should be noted that the invention is not to be limited by the exemplary embodiments shown. In particular, unless explicitly stated otherwise, it is also possible to extract partial aspects of the situation explained in the figures and to combine them with other components and/or findings from other figures and/or the present description. The drawings show the following in schematic form.

DETAILED DESCRIPTION

Figure 1:
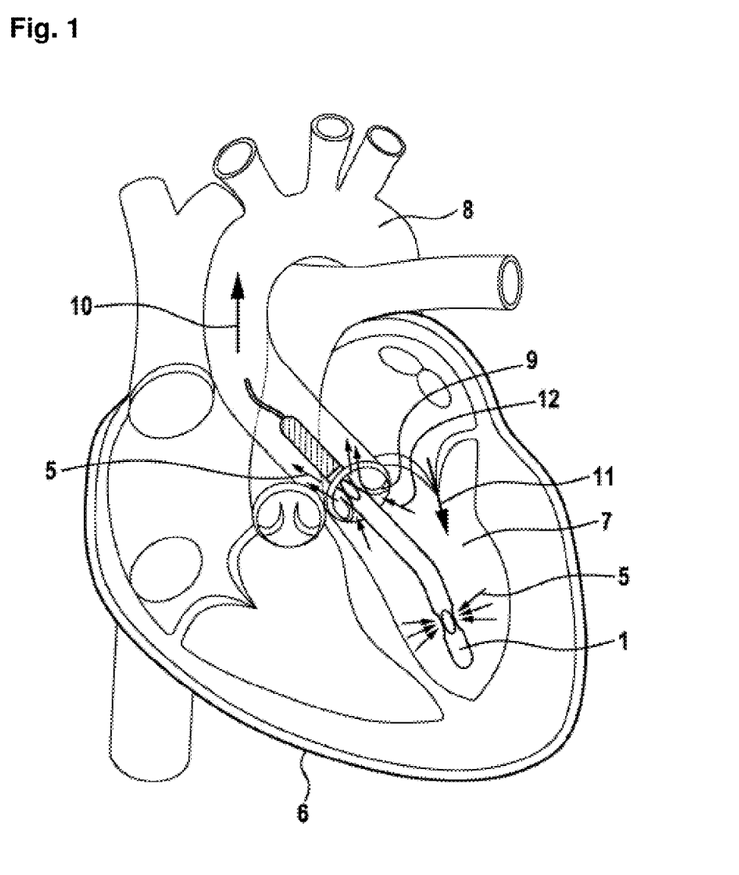
FIG. 1 an implanted vascular assist system in a heart.

FIG. 1 shows in schematic form an implanted vascular (here: ventricular) assist system 1 in a heart 6. The assist system 1 assists the heart 6 by helping to convey blood out of the (left) ventricle 7 into the aorta 8. For this purpose, the assist system 1 is anchored in the aortic valve 9, as illustrated by way of example in FIG. 1. At a level of assist of 100%, the assist system 1 (LVAD) conveys the complete blood volume flow. The level of assist describes the proportion of the volume flow conveyed through a delivery means such as a pump of the assist system 1 or through the assist system 1 to the total volume flow of blood from the ventricle 7 to the aorta 8.

Therefore, at an assist level of 100%, the total fluid volume flow 10 from the ventricle 7, the volume flow 11 from the heart valve into the ventricle 7, and the fluid volume flow 5 through the assist system 1 are identical. In this case, it follows that the aortic valve volume flow or bypass volume flow 12 (formula symbol: $Q_a$) is zero. The total fluid volume flow 10 can also be described as the (total) heart-time volume (HTV, formula symbol: $Q_{HTV}$). The fluid volume flow 5 can also be referred to as a so-called pump volume flow (formula symbol: $Q_p$), which quantifies only the flow through the assist system 1 itself. As a result, the level of assist can be calculated from the ratio $Q_p/Q_{HTV}$.

In the case of lower levels of assist and healthier hearts with a strong ventricular contraction, the heart 6 continues to fulfill its function to a certain extent, so that during systole (heart muscle contracts and pushes the blood out into the aorta 8 as a result of the decrease in volume of the ventricle 7), a pulsatile volume flow component 12 (bypass) is produced by the heart valve or the aortic valve 9. At the same time, the pressure difference in the assist system 1, in particular in the pump typically provided (not shown here) in the assist system 1, drops, so that correspondingly the assist system 1 also conveys an increased amount of fluid volume flow 5 during systole.

Figure 2:
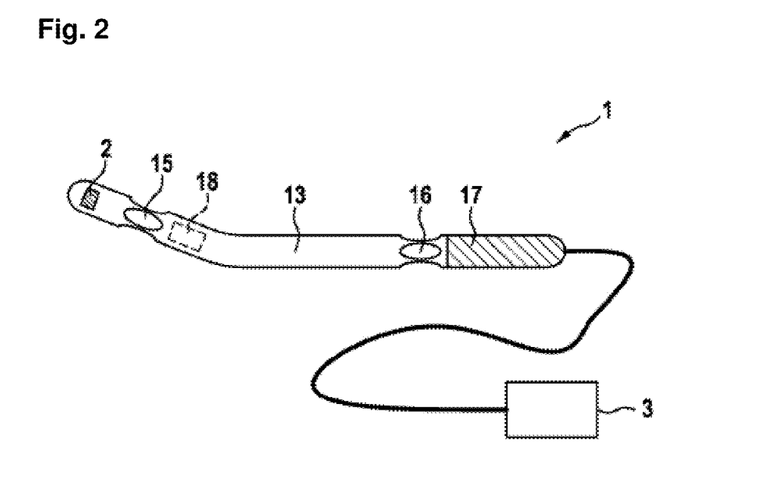
FIG. 2 the assist system from FIG. 1.

FIG. 2 shows in schematic form the assist system 1 from FIG. 1. The assist system 1 comprises an ultrasonic sensor 2, which is designed to carry out pulsed Doppler measurements at different pulse repetition rates, and a processing unit 3 that is designed to determine a flow rate of a fluid (here: blood) flowing through the assist system 1, using the measurement results of the pulsed Doppler measurements at different pulse repetition rates.

In addition, FIG. 2 also shows by way of example that the ultrasonic sensor 2 can be integrated in the tip of a cannula 13 of the assist system 1. The ultrasonic sensor 2 helps to determine the flow rate (amount and at least one direction) of a fluid or fluid volume flow 5, which flows through the assist system 1 and which is also referred to as a pump volume flow ($Q_p$). For this purpose, the ultrasonic sensor 2 is designed to carry out pulsed Doppler measurements in the fluid inside the cannula 13. The fluid can enter the interior of the cannula 13 through one or more inlet openings 15 (from the ventricle 7) and exit through one or more outlet openings 16 (into the aorta 8). In order to assist the fluid flow through the assist system 1, in particular through the cannula 13, the assist system 1 includes here a continuous flow machine 17. The continuous flow machine 17 is generally formed in the manner of a pump. Furthermore, an observation window or a range of measurement 18 of the ultrasonic sensor 2 is also shown by way of example in FIG. 2.

Figure 3:
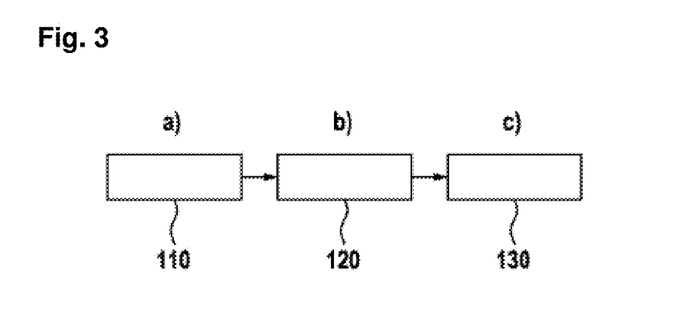
FIG. 3 a sequence of a method presented here in a normal operating mode.

FIG. 3 shows in schematic form a sequence of a method presented here in a normal operating mode. The method is used to determine a flow rate of a fluid flowing through an implanted vascular assist system 1 (see FIGS. 1, 2). The illustrated sequence of process steps a), b), and c) with the blocks 110, 120, and 130 is shown merely for illustrative purposes. In block 110, a first pulsed Doppler measurement is carried out at a first pulse repetition rate by means of an ultrasonic sensor 2 of the assist system 1. In block 120, a second pulsed Doppler measurement is carried out at a second pulse repetition rate by means of the ultrasonic sensor 2 of the assist system 1, where, in this case, the second pulse repetition rate differs from the first pulse repetition rate. In block 130, the flow rate is determined using the measurement results of the first pulsed Doppler measurement and the second pulsed Doppler measurement.

The following parameters are assumed for an exemplary representation of the method:

diameter inlet region or range of measurement, e.g. 5 mm, maximum blood flow to be measured, e.g. Q=9 l/min., resulting maximum blood flow rate: $v_{blood,max}$=7.64 m/s, speed of sound in the blood, e.g. $c_{blood}$=1,540 m/s, ultrasonic frequency, e.g. $f_0$=6 MHZ, distance of the ultrasonic element from the start of the observation window, e.g. 25 mm, number of ultrasonic vibration cycles per emitted ultrasonic PWD pulse, e.g. 10, resulting burst length (in distance): $l_{burst}=c_0 \times 10/f_0$=2.57 mm, resulting maximum propagation distance ultrasonic burst: d=55.13 mm.

The above data gives the following (expected) maximum Doppler shift for a measurement directly in the emission direction (flow direction corresponds to the main emission direction; α=0):

$$df = \frac{2 \cdot v_{blood,max} \cdot f_0}{c_0} = \frac{2 \cdot 7.64 \frac{m}{s} \cdot 6 \text{ MHz}}{1540 \frac{m}{s}} = 59.53 \text{ kHz} \quad (1)$$

The measurement should be carried out as a pulsed Doppler measurement, in which a new ultrasonic pulse is not emitted until an echo of a just previously emitted ultrasonic pulse has decayed. The choice of the pulse repetition rate (PRF) to be used for this purpose is explained below.

Taking into account the (Nyquist) sampling theorem (which, however, does not have to be and is not taken into account in the solution presented here), a maximum Doppler frequency of 59.53 kHz would mean that a minimum pulse repetition rate or a minimum pulse repetition frequency of $$PRFmin = 2 \cdot df = 119.06 \text{ kHz} \quad (2)$$

would have to be observed.

However, in the implanted vascular assist systems that are the focus of the present invention, the following maximum pulse repetition rate $PRF\text{-}_{max\_}$ is calculated from the geometric consideration (maximum propagation distance of the ultrasonic pulse) or the geometric boundary conditions in the assist system and the resulting transit time of all of the relevant signal components:

$$PRF_{max}^{blood} = \frac{c_{blood}}{d} = 27.93 \text{ kHz} \quad (3)$$

Therefore, the maximum pulse repetition rate of the pulsed Doppler measurements here (i.e. for the assist systems that are the focus of the present invention) is smaller than twice the maximum occurring Doppler shift.

These boundary conditions lead to a violation of the sampling theorem and, consequently, to an ambiguity of the measurement results that can be corrected by an evaluation, as described in the following sections.

Figure 4:
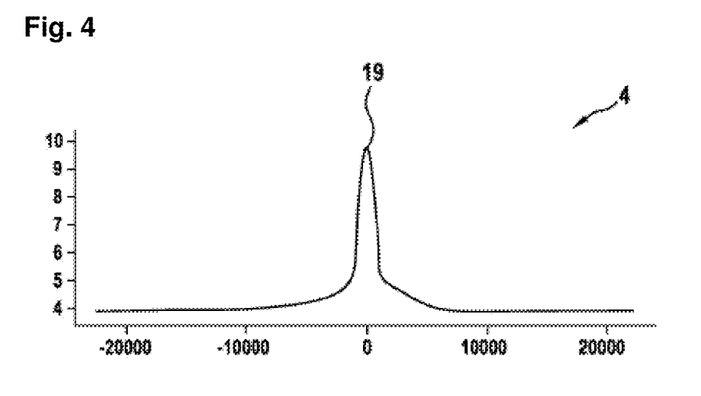
FIG. 4 an exemplary Doppler frequency spectrum.
Figure 5:
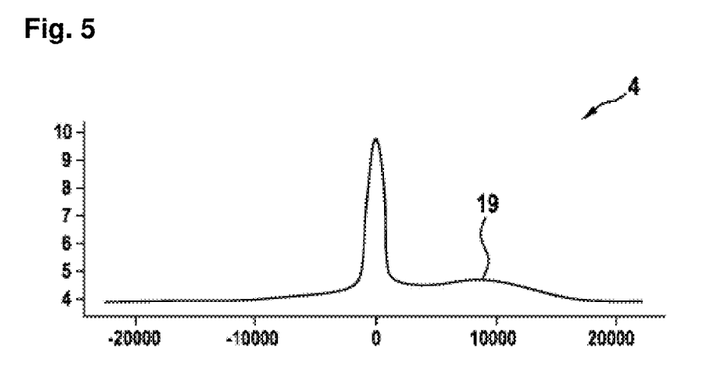
FIG. 5 another exemplary Doppler frequency spectrum.

However, in order to illustrate the problems arising from these boundary conditions, the ambiguity occurring in this case is illustrated in FIGS. 4 and 5 (said ambiguity can be resolved with the solution presented here). FIG. 4 shows in schematic form an exemplary Doppler frequency spectrum 4. FIG. 4 shows a Doppler shift at a pulse repetition rate of approximately 25 KHz. The main frequency component 19 (peak) is below the carrier frequency at approximately 0 Hz. FIG. 5 shows in schematic form another exemplary Doppler shift frequency spectrum 4. FIG. 5 shows a Doppler shift at a pulse repetition rate of approximately 20 kHz. The main frequency component 19 (peak) is at approximately +8 KHz.

In the following sections, an exemplary evaluation of the ambiguous measurement results is described in the context of the solution proposed herein.

Two measurement cycles (sequence of a defined number of ultrasonic pulses emitted in succession) at different PRFs (with respect to the same fluid flow, for example in the same observation window) are included. The actual Doppler shift can be shown as a function of the resulting heart frequency components 19, here peaks $f_1$ and $f_2$:

$$df = f_1 + n_1 \cdot PRF_1 \quad (4)$$

$$df = f_2 + n_2 \cdot PRF_2 \quad (5)$$

This illustrates by way of example how a linear equation system can be set up, in which the Doppler shift df is shown as a function of main frequency components 19, here peaks $f_1$ and $f_2$, of the first pulsed Doppler measurement and the second pulsed Doppler measurement. In addition, this illustrates by way of example a correlation between a detected main frequency component 19 of the Doppler frequency spectrum, here a peak in the Doppler frequency spectrum, a pulsed Doppler measurement, and the pulse repetition rate applied for this Doppler measurement.

By resolving both equations after the Doppler shift df and subsequently equating, the following Diophantine equation is obtained:

$$n_1 \cdot PRF_1 - n_2 \cdot PRF_2 = f_2 - f_1 \quad (6)$$

This illustrates by way of example how a linear Diophantine equation can be set up on the basis of the linear equation system.

At the speed of sound in blood $c_{blood}$, the ultrasonic transmission frequency $f_0$, the flow rate of the blood $v_{blood}$, and an integer pulse repetition rate, an unambiguous solution can be found for this equation.

where $$-|a| \leq n_1 \leq |a| \text{ where } a = \frac{PRF_2}{2 \cdot ggT(PRF_1, PRF_2)} \quad (7)$$

$$-|b| \leq n_2 \leq |b| \text{ where } b = \frac{PRF_1}{2 \cdot ggT(PRF_1, PRF_2)} \quad (8)$$

$$< \frac{a \cdot vPRF_1 \cdot c_0}{2 \cdot f_0} \text{ where } PRF_1 < PRF_2 \quad (9)$$

In this case, the operator ggT represents the largest common divisor. Within these ranges, this equation can be obtained, for example, with the aid of Bezout coefficients or with an exhaustion (brute force) approach.

This procedure is illustrated by way of example with the aid of the values v=8 m/s, $f_0$=4 MHZ, $PRF_1$=11 kHz and $PRF_2$=19 kHz. At these values, the resulting peaks were detected at $f_1$=−2442 Hz and $f_2$=3558 Hz. The resulting Diophantine equation is:

$$n_1 \cdot 11 - n_2 \cdot 19 = 6 \quad (10)$$

The largest common divisor for this case is 1, and the Bezout coefficients are 7 and 4. This gives the following possible solutions:

$$n_1 = 6 \cdot 7 + m \cdot 19 = 4 + m \cdot 19 \quad (11)$$

$$n_2 = 6 \cdot 4 + m \cdot 11 = 2 + m \cdot 11 \quad (12)$$

This illustrates by way of example how the linear Diophantine equation can be solved using Bezout coefficients.

Because a unique solution can be determined only for m=0, only this is considered. It can be used to determine the frequency of the Doppler shift that is now no longer ambiguous. Both equations give the same result.

$$df = f_1 + n_1 \cdot PRF_1 \quad (13)$$

$$= -2442 \text{ Hz} + 4 \cdot 11000 \text{ Hz} = 41558 \text{ Hz} \quad (14)$$

$$df = f_2 + n_2 \cdot PRF_2 \quad (15)$$

$$= -3558 \text{ Hz} + 2 \cdot 19000 \text{ Hz} = 41558 \text{ Hz} \quad (16)$$

The flow rate of the fluid flowing through the assist system 1 (here: blood) can be calculated on this basis by means of the frequency shift due to the Doppler effect:

$$df = f_0 \cdot \frac{2v}{c} \cdot \cos(\alpha)$$

where df is the resulting (unique) Doppler frequency shift; $f_0$ the frequency of the emitted ultrasonic pulse; v the flow rate of the medium (sought here); c the speed of sound in the medium; and a the angle between the ultrasonic sound path and the main flow direction.

In a (ventricular) assist system, v is sought, and α, $f_0$ and c are generally known (at least approximately). It is possible to compensate for the ambiguity usually occurring in such (ventricular) assist systems as discussed above in a particularly advantageous way by means of the solution proposed herein. On the basis of the determined flow rate, the fluid volume flow through the assist system can be determined using the (known) geometric boundary conditions in the assist system (known cross section of the range of measurement or the observation region through which the fluid can flow). Said fluid volume flow can help, at least approximately, to detect the blood volume that is actually conveyed through a (heart) assist system. This knowledge of the volume of blood that is actually pumped by a ventricular assist system or a cardiac assist system is medically of great importance, in particular for controlling the (implanted) assist system.

The solution presented herein makes possible one or more of the following advantages, in particular:

Pulsed Doppler measurement or PWD-based flow rate measurement or volume flow measurement is also made possible even with a large distance between the measurement window and the ultrasonic transducer.

Resolution of the geometrically induced ambiguity of the Doppler shift on the basis of geometric boundary conditions in the assist system.

The invention claimed is:

1. A method for determining a flow rate v of blood flowing through a cardiac assist system, comprising:
    performing a first pulsed Doppler measurement at a first pulse repetition rate $PRF_1$ using an ultrasonic sensor of the cardiac assist system;
    performing a second pulsed Doppler measurement at a second pulse repetition rate $PRF_2$ using the ultrasonic sensor of the assist system, wherein the second pulse repetition rate $PRF_2$ is greater than the first pulse repetition rate $PRF_1$; and
    determining the flow rate using measurement results of the first pulsed Doppler measurement and the second pulsed Doppler measurement by solving for an integer $n_1$, an integer $n_2$, and a main component $f_1$ of the first pulsed Doppler measurement and a main component $f_2$ of the second pulsed Doppler measurement using a linear Diophantine equation, wherein the linear Diophantine equation comprises:

$$n_1 \cdot PRF_1 - n_2 \cdot PRF_2 = f_2 - f_1$$

for a boundary condition of:

$$v < \frac{a \cdot PRF_1 \cdot c_0}{2 f_0}$$

assuming $$-|a| \leq n_1 \leq |a| \text{ and } -|b| \leq n_2 \leq |b|,$$

wherein $$a := \frac{PRF_2}{2 \cdot ggT(PRF_1, PRF_2)} \text{ and } b := \frac{PRF_1}{2 \cdot ggT(PRF_1, PRF_2)},$$

wherein ggT ($PRF_1$, $PRF_2$) comprises the largest common divisor of $PRF_1$ and $PRF_2$,
    and wherein $f_0$ comprises the ultrasonic transmission frequency of the ultrasonic sensor and $c_0$ comprises a speed of sound in the blood.

2. The method of claim 1, wherein at least one of performing a first pulsed doppler measurement and performing a second pulsed doppler measurement comprises emitting a new ultrasonic pulse using an ultrasonic element only after an echo of an immediately previously emitted ultrasonic pulse has been received by the ultrasonic sensor.

3. The method of claim 1, wherein $PRF_1$ or $PRF_2$ is smaller than twice a maximum occurring Doppler shift.

4. The method of claim 1, wherein determining the flow rate comprises using a correlation between a detected main frequency component of the Doppler frequency spectrum of the first pulsed Doppler measurement and the first pulse repetition rate $PRF_1$ or the second pulsed Doppler measurement and the second pulse repetition rate $PRF_2$.

5. The method of claim 1, wherein determining the flow rate comprises solving the linear Diophantine equation using Bezout coefficients or an exhaustion method.

6. The method of claim 1, wherein an observation window of the ultrasonic sensor is in a range of 25 mm to 55 mm from an ultrasonic element of the ultrasonic sensor.

7. A cardiac assist system comprising:
    an ultrasonic sensor configured to perform a first pulsed Doppler measurement at a first pulse repetition rate $PRF_1$ and a second pulsed Doppler measurement at a second pulse repetition rate $PRF_2$, wherein $PRF_2$ is greater than $PRF_1$; and
    a processing unit configured to:
    determine a flow rate of a fluid flowing through the cardiac assist system using measurement results of the first pulsed Doppler measurement and the second pulsed Doppler measurement,
    wherein determining the flow rate using the measurement results of the first pulsed Doppler measurement and the second pulsed Doppler measurement comprises solving for an integer $n_1$, an integer $n_2$ and a main component $f_1$ of the first pulsed Doppler measurement and a main component $f_2$ of the second pulsed Doppler measurement using a linear Diophantine equation comprising:

$$n_1 \cdot PRF_1 - n_2 \cdot PRF_2 = f_2 - f_1$$

for the boundary condition:

$$v < \frac{a \cdot PRF_1 \cdot c_0}{2 f_0}$$

assuming:

$$-|a| \leq n_1 \leq |a| \text{ and } -|b| \leq n_2 \leq |b|,$$

wherein $$a := \frac{PRF_2}{2 \cdot ggT(PRF_1, PRF_2)} \text{ and } b := \frac{PRF_1}{2 \cdot ggT(PRF_1, PRF_2)},$$

wherein ggT ($PRF_1$, $PRF_2$) comprises the largest common divisor of $PRF_1$ and $PRF_2$,
    and wherein $f_0$ is the ultrasonic transmission frequency of the ultrasonic sensor and $c_0$ is a speed of sound in the fluid.

8. The cardiac assist system of claim 7, wherein the processing unit is configured to solve the linear Diophantine equation using Bezout coefficients or an exhaustion method to determine the flow rate.

9. The cardiac assist system of claim 7, wherein the processing unit is configured to calculate a fluid flow based on the flow rate.

10. The system of claim 7, wherein the ultrasonic sensor comprises an observation window in a range of 25 mm to 55 mm from an ultrasonic element of the ultrasonic sensor.

11. The system of claim 7, further comprising a cannula, wherein the ultrasonic sensor is configured to perform the first pulsed Doppler measurement and the second pulsed Doppler measurement within the cannula.

12. The system of claim 11, wherein the ultrasonic sensor is integrated into the tip of the cannula.

13. A method for determining a fluid flow through a cardiac assist system comprising:

determining a flow rate v of blood flowing through the cardiac assist system, wherein determining the flow rate v comprises:

performing a first pulsed Doppler measurement at a first pulse repetition rate $PRF_1$ using an ultrasonic sensor of the cardiac assist system;

performing a second pulsed Doppler measurement at a second pulse repetition rate $PRF_2$ using the ultrasonic sensor of the assist system, wherein the second pulse repetition rate $PRF_2$ is greater than the first pulse repetition rate $PRF_1$; and determining the flow rate using measurement results of the first pulsed Doppler measurement and the second pulsed Doppler measurement by solving for an integer $n_1$, an integer $n_2$, and a main component $f_1$ of the first pulsed Doppler measurement and a main component $f_2$ of the second pulsed Doppler measurement using a linear Diophantine equation, wherein the linear Diophantine equation comprises:

$$n_1 \cdot PRF_1 - n_2 \cdot PRF_2 = f_2 - f_1$$

for a boundary condition of:

$$v < \frac{a \cdot PRF_1 \cdot c_0}{2 f_0}$$

assuming $-|a| \leq n_1 \leq |a|$ and $-|b| \leq n_2 \leq |b|$, wherein $$a := \frac{PRF_2}{2 \cdot ggT(PRF_1, PRF_2)} \text{ and } b := \frac{PRF_1}{2 \cdot ggT(PRF_1, PRF_2)},$$

wherein ggT ($PRF_1$, $PRF_2$) comprises the largest common divisor of $PRF_1$ and $PRF_2$, and wherein $f_0$ comprises the ultrasonic transmission frequency of the ultrasonic sensor and $c_0$ comprises a speed of sound in the blood; and determining the fluid flow in the cardiac assist system based on the flow rate v.

* * * * *